United States Patent [19]

Bod et al.

[11] Patent Number: 4,731,479

[45] Date of Patent: Mar. 15, 1988

[54] N-SULFAMYL-3-HALOPROPIONAMIDINES

[75] Inventors: Péter Bod, Gyömrö; Kálmán Harsányi, Budapest; Eva Agai née Csongor, Budapest; Erik Bogsch, Budapest; Éva Fekecs, Budapest; Ferenc Trischler, Budapest; György Domány, Budapest; István Szabadkai, Budapest; Béla Hegedüs, Budapest, all of Hungary

[73] Assignee: Richter Gedeon Vegyeszeti Gyar Rt., Budapest, Hungary

[21] Appl. No.: 905,833

[22] Filed: Sep. 10, 1986

[30] Foreign Application Priority Data

Sep. 11, 1985 [HU] Hungary .................... 3423/85

[51] Int. Cl.[4] .................... C07C 143/72
[52] U.S. Cl. .................... 564/79
[58] Field of Search .................... 564/79

[56] References Cited

U.S. PATENT DOCUMENTS 3,121,084  2/1964  Winberg .................... 564/79

FOREIGN PATENT DOCUMENTS 905408  12/1986  Belgium .

OTHER PUBLICATIONS

Wagner et al, "Synthetic Organic Chemistry", (1953), p. 635.
Richter, "Text Book of Organic Chemistry," (1952), p. 216.

Primary Examiner—Anton H. Sutto
Attorney, Agent, or Firm—Karl F. Ross; Herbert Dubno; Jonathan Myers

[57] ABSTRACT

The invention relates to new propionamidine derivatives of formula (I)

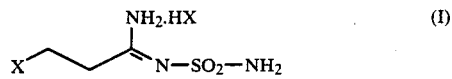

wherein
X is halogen, and to a process for their preparation. According to the invention compounds of the formula (I) are prepared by reacting a 3-halopropionitrile of the formula (III)

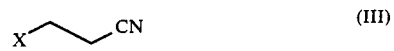

wherein
X is as defined above, with sulfamide of the formula (II)

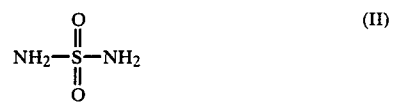

in the presence of a hydrogen halide.

Compounds of the formula (I) are useful intermediates in the preparation of famotidine.

1 Claim, No Drawings

N-SULFAMYL-3-HALOPROPIONAMIDINES

The invention relates to new propionamidine derivatives of the formula (I)

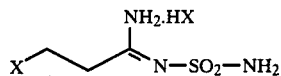
(I)

wherein
X is halogen.

The new compounds of the formula (I) are useful intermediates in the preparation of famotidine [N-sulfamyl-3-(2-guanidino-thiazol-4-yl-methylthio)-propionamidine], an anti-ulcer agent providing excellent results in the treatment of gastric and intestinal ulceration.

According to another aspect of the invention there is provided a process for the preparation of the compounds of formula (I).

Compounds of the formula (I) are new. A structurally related compound, N-sulfamylacrylamidine (compound of formula (IV))

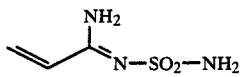
(IV)

is e.g. disclosed in the U.S. Pat. No. 4,496,737, where it is prepared starting from 3-methylthio-propionitrile by a long and cumbersome four-step synthesis, with a total yield of 5.5%. In addition to the extremely low yield by which it can be prepared a further disadvantage of this compound is that its purification is very difficult even by chromatography. Accordingly, its use in the preparation of famotidine does not make possible an industrially applicable, economic synthesis.

The target of the present invention is to provide new intermediates from which famotidine can be prepared economically.

We have experimentally found that the N-sulfamyl-3-halopropionamidine derivative of the formula (I), wherein X is as defined above, are easy to prepare and can easily be converted into famotidine.

According to the invention the new propionamidine derivatives of the formula (I), wherein X is as defined above, are prepared by reacting a 3-halopropionitrile of the formula (III)

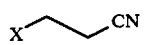
(III)

wherein X is as defined above, with sulfamide of the formula (II)

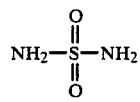
(II)

in the presence of a hydrogen halide.

According to a preferred embodiment of the invention a 3-halopropionitrile is prepared in situ from acrylonitrile by addition with a hydrogen halide (e.g. with gaseous hydrogen chloride or hydrogen bromide).

According to the invention the new compounds of the formula (I) can for example be prepared by introducing dry hydrogen chloride gas into a stirred solution of the sulfamide in an excess of 3-chloropropionitrile (or acrylonitrile). The precipitated cyrstalline compound of the formula (I) is filtered off upon cooling and optionally after dilution with an organic solvent, washed with acetone and dried.

Favorable results are obtained by reacting 1 mole of sulfamide with 1.5 to 8 moles, preferably 1.8 to 2.5 moles, of a 3-halopropionitrile derivative of the formula (III), at 10° C. to 100° C., preferably 10° C. to 60° C., for 1 to 100, preferably 20 to 60 hours, while a hydrogen halide is passed through the solution. Solvents, e.g. ethers, may be used.

The main advantages of the process according to the invention are as follows:

(a) due to the direct sulfamide nitrile addition the isolation and reaction of the iminoether base intermediate, which is subject to decomposition, can be avoided together with the purification problems;

(b) the reaction partners of sulfamide (3-chloropropionitrile or acrylonitrile and hydrogen chloride gas) are readily accessible, cheap industrial raw materials;

(c) the product is not hygroscopic, well crystallizable, is easy to filter and is obtained with a yield of at least 70%;

(d) the N-sulfamyl-3-halopropionamidine salts prepared according to the invention can be converted into famotidine by reaction with S-(2-guanidino-thiazol-4-yl-methyl)-isothiurea easily, with an excellent yield. More particularly, famotidine is prepared starting from the new intermediates according to the invention by S-alkyalting 2-guanidino-thiazol-4-yl-methyl-urea with the N-sulfamyl-3-halopropionamidine dihydrohalides of the formula (I), wherein X is as described above. The yields obtained by this process are high (around 70%).

A further advantage of the process according to the invention is that the halopropionitrile used in an excess amount or formed can be easily recovered and recycled into the process.

Further details of the invention are illustrated by the aid of the following non-limiting Examples.

EXAMPLE 1

N-Sulfamyl-3-chloropropionamidine hydrochloride

To a suspension of 9.61 g. (0.10 mole) of sulfamide in 60 ml (68 g., 0.76 mole) of 3-chloropropionitrile dry hydrogen chloride gas is introduced under stirring at 50° to 60° C. for 5 hours. The gain in weight is about 9 to 12 g. The reaction mixture is then cooled with ice water for one hour, the product is filtered off, washed twice with acetone and dried up to steady weight.

Yield: 14.9 g. (67.1%)
Melting point: (142°)–144°–146° C. (decomp.)
Analysis: calculated: C 16.24%, H 4.08%, Cl 31.90%, N 18.92%; found: C 16.30%, H 4.13%, Cl 31.86%, N 18.90%.

Purity: 97.0% (determined by potentiometric titration in a methanolic medium)

IR spectrum (in KBr tablet, determined on a "Perkin-Elmer 257" equipment):
$C=N$—1675 cm$^{-1}$),
$SO_2$—1170 cm$^{-1}$ br,
C-Cl—660 cm$^{-1}$.

Protone NMR spectrum (d$_6$-DMSO/D$_2$O, determined on a "Varian EM 360" epuipment):

| | | |
|---|---|---|
| =C—CH$_2$— | 3.05 ppm | t |
| Cl—CH$_2$— | 4.00 ppm | t |
| X—H | 8.5 ppm | s(b)* |

EXAMPLE 2

N-Sulfamyl-3-chloropropionamidine hydrochloride

To a stirred suspension of 9.61 g. (0.10 mole) of sulfamide in 30 ml (34 g., 0.38 mole) of 3-chloropropionitrile hydrogen chloride gas is introduced, as described in Example 1. After cooling with ice water for one hour the reaction mixture is diluted with 30 ml of dry ethyl ether, the product is filtered off, washed twice with acetone and dried.

Yield: 16.15 g. (72.7%)

Melting point: (142°)–144°–146° C. (decomp.)

EXAMPLE 3

N-Sulfamyl-3-chloropropionamidine hydrochloride 18 to 20 g. of hydrogen chloride gas are absorbed in a stirred suspension of 9.61 g. sulfamide in 27 g. (34 ml, 0.5 mole) of acrylonitrile to 0° to 2° C. The reaction mixture is then heated up to 50° C. and hydrogen chloride gas is passed through it for three hours, while the inner temperature is kept between 50° C. and 60° C. The thick, white crystal suspension obtained is cooled to room temperature, diluted with 25 ml of isopropyl ether, cooled with ice water, filtered, washed with acetone and dried.

Yield: 16.0 g. (72.0%)

Melting point: (143°)–145°–147° C. (decomp.)

EXAMPLE 4

N-Sulfamyl-3-chloropropionamidine hydrochloride

A suspension of 9.61 g. of sulfamide with 26.9 g. (24.0 ml, 0.30 mole) of regenerated 3-chloropropionitrile and 10.7 g. (23.5 ml, 0.2 mole) of acrylonitrile is stirred continuously whereupon 7 to 8 g. of hydrogen chloride gas are absorbed in the suspension at a temperature of 0° to +2° C. The mixture is then heated up to 50° C., and hydrogen chloride gas is passed through it for further 3 hours, at a temperature of 50° to 60° C. After dilution with 25 ml of isopropyl ether and cooling with ice the product obtained is filtered off, washed with acetone and dried.

Yield: 15.5 g. (69.8%)

Melting point: (143°)–144°–146° C. (decomp.)

We claim:

1. Propionamidine derivatives of the formula (I)

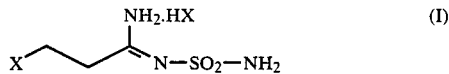

wherein X is halogen.